US00PP20027P3

(12) United States Plant Patent
Lyrene

(10) Patent No.: US PP20,027 P3
(45) Date of Patent: May 26, 2009

(54) 'SWEETCRISP' SOUTHERN HIGHBUSH BLUEBERRY PLANT

(50) Latin Name: *Vaccinium corybosum*
Varietal Denomination: Sweetcrisp

(75) Inventor: Paul M. Lyrene, Gainesville, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 177 days.

(21) Appl. No.: 11/288,767

(22) Filed: Nov. 30, 2005

(65) Prior Publication Data

US 2007/0124841 P1 May 31, 2007

(51) Int. Cl.
*A01H 5/00* (2006.01)

(52) U.S. Cl. ..... Plt./157

(58) Field of Classification Search ..... Plt./157
See application file for complete search history.

*Primary Examiner*—Kent L Bell
(74) *Attorney, Agent, or Firm*—Jondle & Associates, P.C.

(57) ABSTRACT

A new and distinct low-chill southern highbush (*Vaccinium corymbosum*) cultivar. Its novelty lies in the following unique combination of features.

1. Has a chilling requirement of only 200 to 300 hrs. below 7° C.
2. Produces a vigorous bush with good survival in the field.
3. Produces berries that are unusually sweet and firm.

4 Drawing Sheets

4. Latin name of the genus and species. *Vaccinium corymbosum* L.
5. Variety denomination. 'Sweetcrisp'.

6. BACKGROUND OF THE INVENTION

The invention relates to a new and distinct variety of southern highbush blueberry (*Vaccinium corymbosum* L) hybrid named 'Sweetcrisp.' 'Sweetcrisp' is a southern highbush blueberry clone distinguished by its low chilling requirement, its vigorous, disease-resistant bush, and by its very firm sweet berries that ripen from late April through mid-May when grown in north Florida. Several hundred plants of 'Sweetcrisp' have been propagated by softwood cuttings at Gainesville, Fla. and the resulting plants have all been phenotypically indistinguishable from the original plant. Contrast is made to 'Star' (U.S. Plant Pat. No. 10,675), an important variety widely planted in Florida and Georgia for early-season blueberry production. The new variety is important because it produces a firmer, sweeter berry than 'Star' and is resistant to cane canker disease (caused by *Botryosphaeria corticis*), to which 'Star' is susceptible.

7. BRIEF SUMMARY OF THE INVENTION

'Sweetcrisp', when grown in north Florida, is distinguished from all other blueberry plants known by the inventor by the following combination of characteristics: very low chilling requirement; high vigor and early leafing; early ripening (50% ripe berries in north Florida ripen by April 28, about the same as for 'Star'); and berries that are very sweet and very firm.

8. ORIGIN OF THE VARIETY

'Sweetcrisp' originated as a seedling from the cross 'Southern Belle' (U.S. Plant Pat. No. 13,931)×FL95-3 (unpatented) made as part of the University of Florida breeding program in a greenhouse at Gainesville, Fla. in March, 1996. The seedling was first fruited in a high-density field nursery in the spring of 1998. After the second fruiting, which was observed in the field in the spring of 1999, 'Sweetcrisp' was propagated by softwood cuttings in June, 1999, and a 20-plant plot was established in a test plot in a commercial field at Windsor, Fla. March, 2001. Because the plants were very vigorous and resistant to stem blight and root rot and produced berries that were unusually firm and sweet, the plant was again propagated by cuttings, and 50 additional plants were planted in a second test plot at the same farm in March 2003. Several hundred additional plants were established at a test site in Archer, Fla. January 2004.

9. BRIEF DESCRIPTION OF THE DRAWING

The color chart used in this specification is "The Pantone Book of Color", by Leatrice Eiseman and Lawrence Herbert. 1990. Harry N. Abrams, Inc., Publishers, N.Y. Where colors in the drawings differ from the Pantone color designations in the verbal descriptions, the Pantone color designations are accurate.

10. DETAILED BOTANICAL DESCRIPTION

Figure 1:
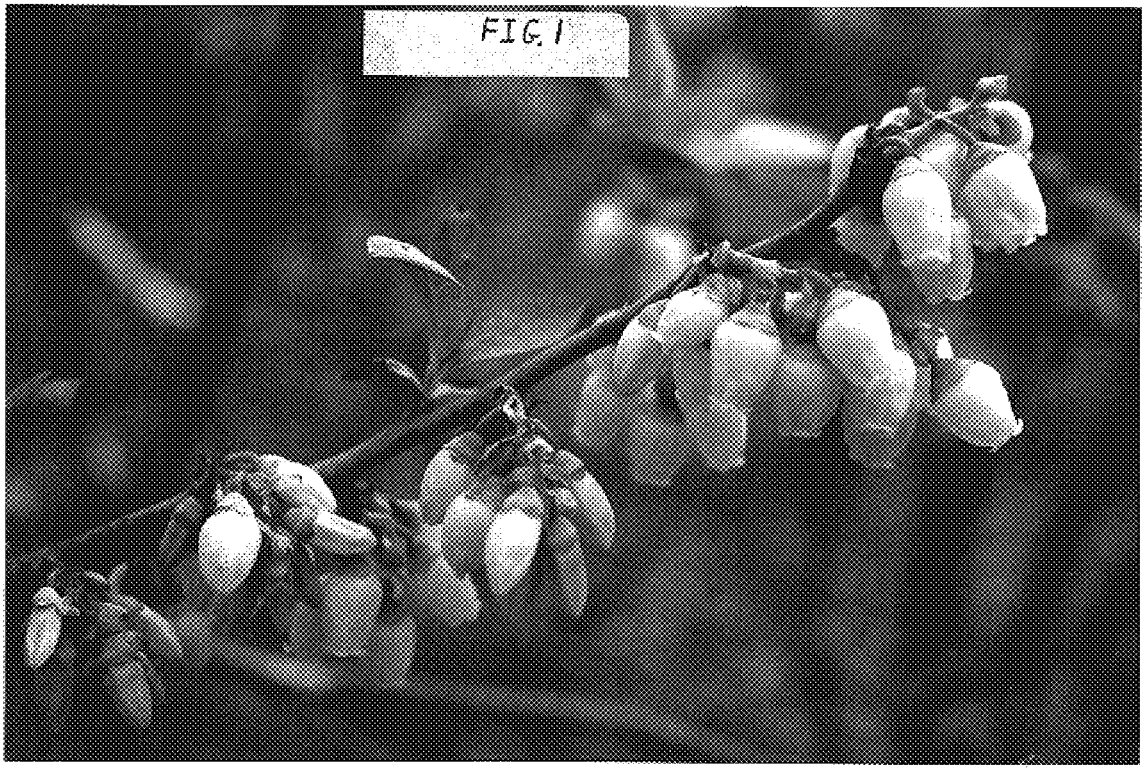
FIG. 1 shows a flowering branch of 'Sweetcrisp' in the field. Cold weather imparts a pink tinge to the corollas of the unopened flowers.
Figure 2:
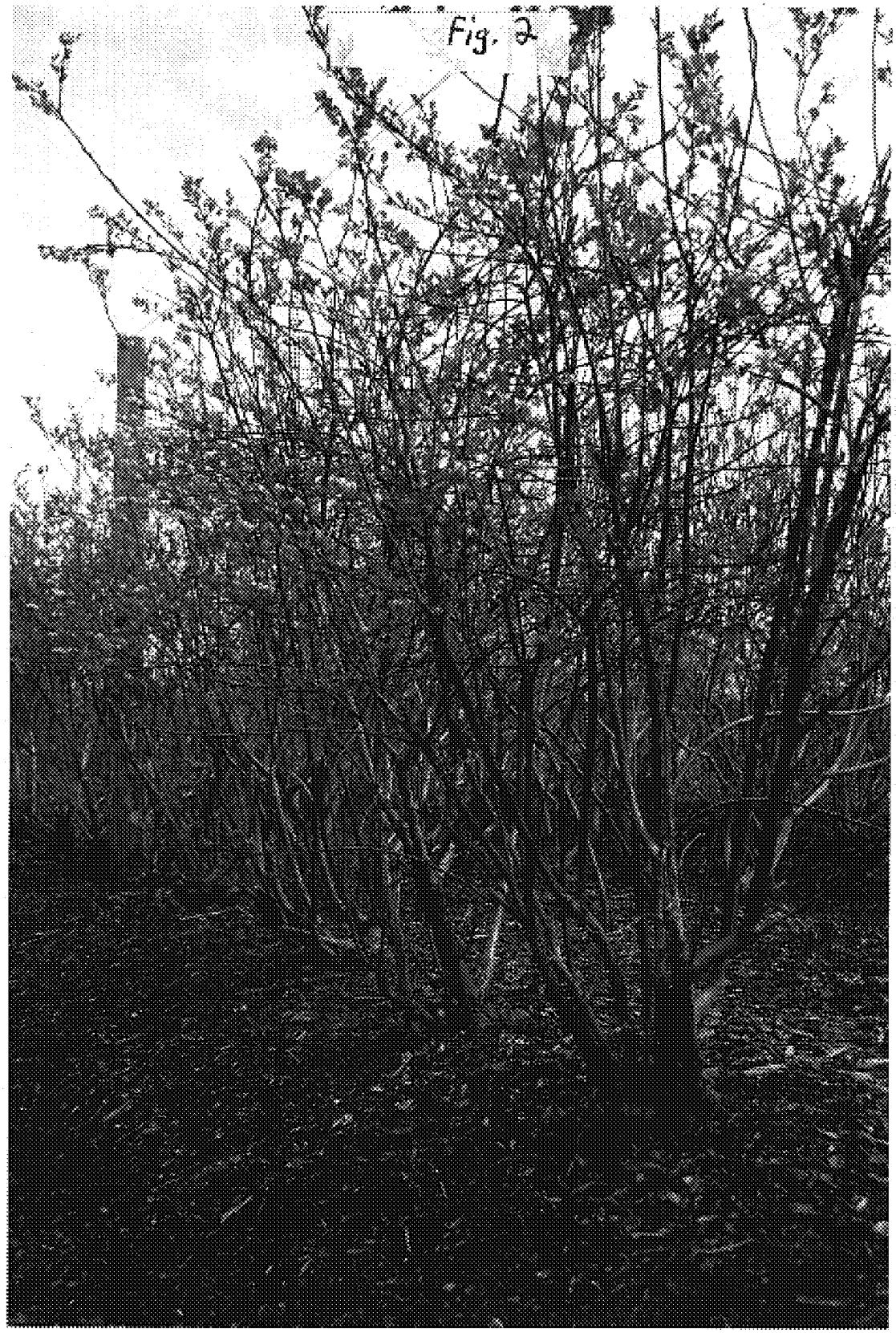
FIG. 2 shows a row of 4-year old plants showing the vigorous, upright growth habit.
Figure 3:
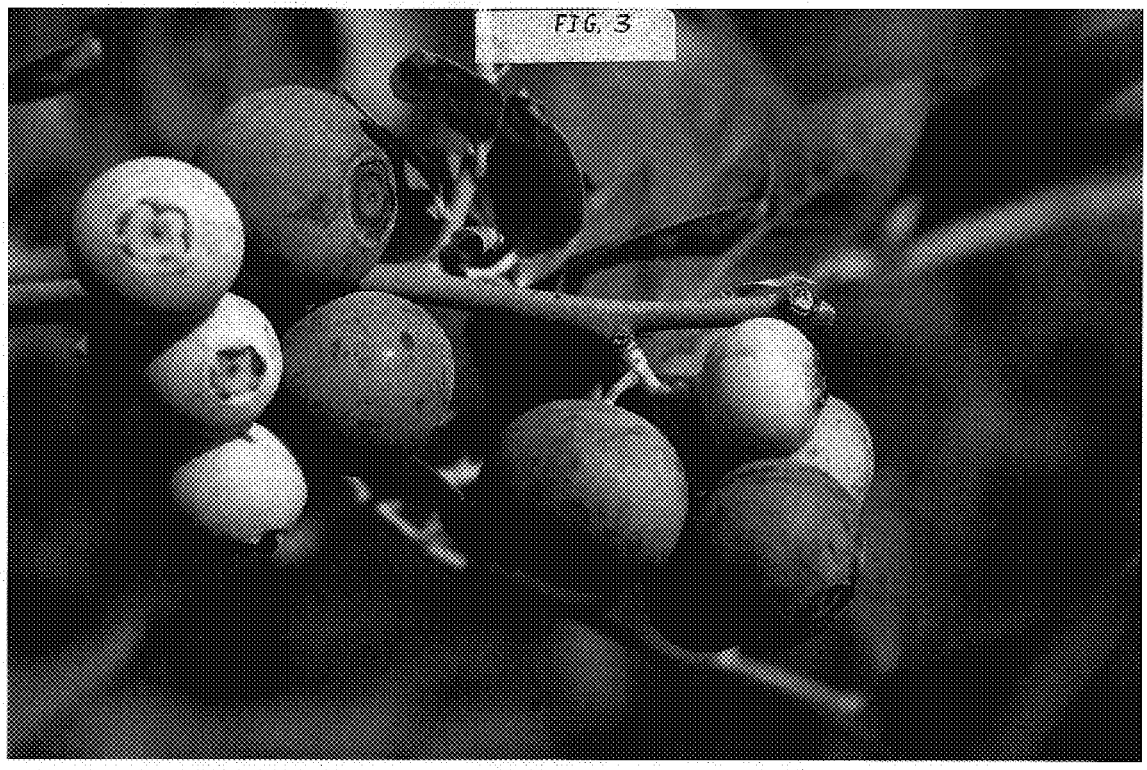
FIG. 3 shows clusters containing mature and immature berries on a field-grown plant.
Figure 4:
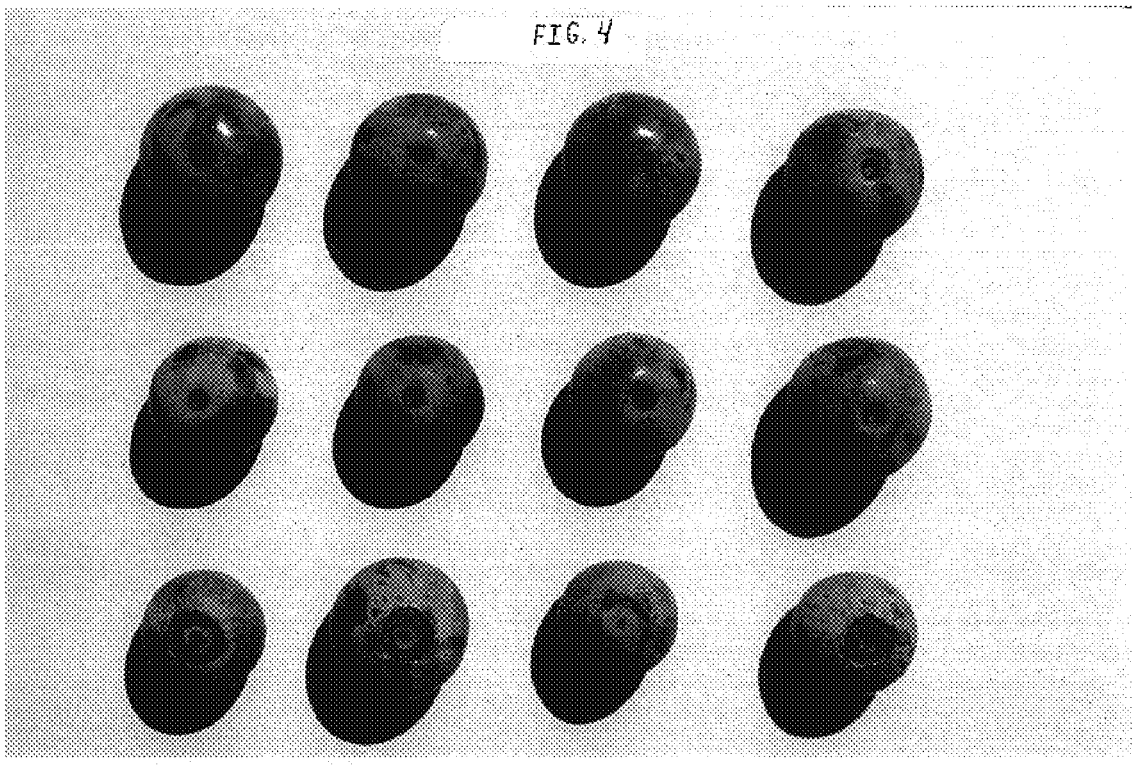
FIG. 4 shows berries at close range. The small, dry picking scar and relatively undeveloped calyx lobes are visible.

The following descriptions relate to plants grown in the field in north Florida (Windsor, Fla.). Color designations are from "The Pantone Book of Color" (by Leatrice Eiseman and Lawrence Herbert; Harry N. Abrams, Inc., Publishers, New York, 1990). Where the Pantone color designations differ from the colors in the Drawings, the Pantone colors are accurate.

MARKET CLASS

'Sweetcrisp' produces southern highbush blueberries suitable for both the fresh and processed fruit markets.

Bush: Bush characteristics were taken from a plot of twenty 4-year-old plants growing in a test plot in a commercial field near Windsor in northeast Florida.

*Plant height.*—2.0 m.

*Canopy diameter measured at widest part of the bush.*—2.0 m.

*Plant vigor.*—High. More vigorous and faster growing than 'Star'.

*Growth habit.*—Between upright and spreading.

*Flower bud density (number) along flowering twigs in January.*—Medium.

*Twigginess.*—Medium.

*Tendency toward evergreenness.*—Medium.

Trunk and branches:

*Suckering tendency.*—Medium. Four-year-old plants have an average of 7 major canes rising from a crown 30 cm in diameter.

*Surface texture of strong, 1-year-old shoots observed in mid-December.*—Smooth.

*Surface texture of strong, 1-year-old wood observed in December.*—Smooth.

*Surface texture of 3-year-old and older wood.*—Rough, exfoliating, producing vertical cracks.

*Color of new twigs observed in mid-December in the field.*—"Leek Green", Pantone 15-0628.

*Color of 1-year-old, rough bark observed in mid-December.*—"Peach Bloom", Pantone 15-1327.

*Color of 3-year-old rough-textured canes.*—"Sheer Pink", Pantone 12-1106.

*Internode length on strong, upright shoots measured Feb. 1.*—1.4 cm.

Leaves:

*Leaf length including petiole, from tip of petiole to end of blade.*—Median 54 mm.

*Leaf width at widest point.*—Median 30 mm.

*Petiole length.*—6.0 mm.

*Petiole diameter.*—2.0 mm.

*Petiole color.*—"Pale Blush", Pantone 14-1312.

*Leaf shape.*—Ovate, terminating in a very short dew tip, 0.2 mm long, which is visible with a 15X microscope.

*Leaf apex.*—Acute.

*Leaf base.*—Acute.

*Leaf margin.*—Entire, except minutely serrate with sessile glands along the margin of the petiolar half of the leaf blades. These glands are visible at 30X magnification.

*Color of upper surface of leaves.*—"Loden Green", Pantone 18-0422.

*Color of lower surface of leaves.*—"Boa", Pantone 17-0625.

*Pubescence on upper surface of leaves.*—Midribs and major veins have a dense indumentum of short, white, curly hairs visible at 30X magnification. Otherwise glabrous.

*Pubescence on lower surface of leaves.*—Midribs and major veins have a sparse indumentum of short, white, curly hairs. Otherwise glabrous.

*Pubescence on leaf margins.*—Minutely serrate with sessile glands along the margins of the petiolar half of the leaf blades. These glands are visible at 30X magnification.

*Relative time of leafing vs. flowering.*—In commercial fields in North Florida, where it is sprayed with hydrogen cyanomide in midwinter, 'Sweetcrisp' normally produces new leaves before it flowers. With respect to this desirable behavior, it is equal to 'Star' and surpasses most other commercial highbush cultivars grown in Florida.

Flowers:

*Flower arrangement.*—Flowers arranged alternately along a short, leafless, deciduous branch.

*Fragrance.*—Little or none.

*Pedicel length at time of anthesis.*—Median=4 mm.

*Pedicel diameter at time of anthesis.*—1 mm.

*Peduncle length at time of anthesis.*—Highly variable; median=6 mm.

*Peduncle diameter at time of anthesis.*—1.5 mm.

*Flower shape.*—Urceolate.

*Pollen staining with 2% acetocarmine.*—This is a measure of potential pollen fertility. 95%. The pollen includes some tetrads in which one or two spores have aborted. Although pollen staining appears to be slightly below normal, pollen fertility is not expected to be a problem in commercial fields.

*Abundance of pollen shed.*—High.

*Color of dried pollen.*—"Yolk Yellow", Pantone 14-0846.

*Flower length, pedicel attachment point to corolla tip excluding the pedicel.*—11 to 12 mm.

*Flower petals.*—The flowers have 5 petals, which are fused into a tubular corolla. For the length, diameter, color and texture of the petals see description of corolla.

*Length of corolla tube.*—9 mm.

*Diameter of corolla tube at widest point.*—6 to 7 mm.

*Style length.*—Top of ovary to stigma tip. 8 mm.

*Calyx cup diameter at anthesis.*—Tip of lobe to tip of opposite lobe. 5 mm. Calyx lobes are unusually short for a southern highbush blueberry cultivar.

*Corolla aperture diameter.*—3 mm.

*Calyx surface.*—Smooth.

*Corolla color at anthesis.*—"Parchment", Pantone 13-0908.

*Corolla surface texture.*—Smooth.

*Calyx color at anthesis.*—"Peridot", Pantone 17-0336.

*Pistil color at anthesis.*—"Herbal Green", Pantone 15-0336.

*Pedicel and peduncle color.*—"Periodot", Pantone 17-0336.

*Flowering period.*—Mean date of 50% open flower at Windsor, Fla. Feb. 17. Averages 10 days before 'Star'. In North-central Florida, flowering time varies depending on weather, but most flowers open between Feb. 1 and March 1.

*Flower cluster (tight, medium, loose).*—Loose.

*Pedicel length on ripe berry.*—Median 5 mm.

*Pedicel diameter on ripe berry.*—1 mm.

*Peduncle length on ripe berry clusters.*—Highly variable. Median about 10 mm.

*Peduncle diameter on ripe berry clusters.*—1.5 mm.

*Number of flowers per cluster.*—Median=5.

*Location of tip of stigma relative to lip of the corolla.*—Stigma tip is about 1 mm inside of the end of the corolla tube. In other words, if the style were 1 mm longer, the stigma tip would extend just to the outer edge of the corolla tube.

*Self fruitfulness.*—Partially but not completely self-fruitful. Fruit set after hand emasculation and self-pollination in the greenhouse is about 50% but berry size is considerably reduced compared to berries resulting when flowers are cross pollinated.

Berry:

*Mean date of first commercial harvest* (25% *of berries ripe*).—April 26.

*Mean date of mid-harvest.*—May 2.

*Mean date of last harvest.*—May 20.

*Diameter of calyx aperture on mature berry.*—7 mm.

*Calyx lobes on mature berry.*—Size and shape. Very small. Calyx dish very shallow and wide.

*Berry cluster* (*tight, medium, or loose*).—Loose.

*Pedicel length on ripe berry* 5 *mm.*—Peduncle length on ripe berry. Variable, typically about 10 mm.

*Number of berries per cluster.*—Median 5.

*Detachment force for ripe berries.*—Medium to low.

*Mean berry weight on well-pruned plants.*—2.3 g per berry compared to 1.8 for 'Star'.

*Mean berry height.*—14 to 15 mm.

*Mean berry width.*—15 mm.

*Berry shape.*—Oblate.

*Surface color of mature berries while on the plant.*—"Storm Gray", Pantone 15-4003.

*Surface color of the berries after harvesting and packing.*—"Frost Gray", Pantone 17-0000.

*Surface color of ripe berry after polishing.*—"Jet Black", Pantone 19-0303.

*Internal flesh color of ripe berry.*—"Frozen Dew", Pantone 13-0513.

*Berry surface wax.*—Medium in amount and in persistence during handling of the berry.

*Berry pedicel scar.*—Very small and dry.

*Berry firmness.*—Very high.

*Berry flavor.*—Very sweet and low in acidity.

*Berry texture.*—Good: small seeds, very juicy, thin skin.

*Color of dried seeds.*—"Hazel", Pantone 17-1143.

*Weight of well-developed dried seeds.*—0.49 mg per seed.

*Length of well-developed, dried seeds.*—Mean=1.9 mm.

*Width of well-developed, dried seeds.*—Mean=1.0 mm.

Physiological characteristics:

*Chilling requirement.*—200–300 hours below 7° C.

*Cold hardiness.*—Flowers and fruit are hardy to −3° C. The plant, during winter dormancy, is hardy to −15° C.

*Productivity.*—In northeast Florida, 'Sweetcrisp' produces about 5 pounds of berries per bush on plants 3 years old or older.

*Ease of propagation.*—'Sweetcrisp' is easy to propagate from softwood cuttings. The plants survive and grow well in nursery beds.

Resistance to diseases, insects, and mites:

'Sweetcrisp' has grown vigorously and show excellent bush survival in the field. It appears to have above-average resistance to root rot (*Phytophthora cinnamomi*) and stem blight (*Botryosphaeria dothidia*). The plants have shown no signs of cane canker (*Botryosphaeria corticis*) susceptibility in the field. The fungal leaf spots that are common on highbush blueberries grown in Florida are easily controlled by approved fungicides.

Comparison to parental cultivars:

'Sweetcrisp' differs from the female parent 'Southern Belle' (U.S. Plant Pat. No. 3,931), in that 'Sweetcrisp' is much more vigorous and faster growing than 'Southern Belle'. 'Sweetcrisp' has a lower chill requirement and survives better in the field than 'Southern Belle'. In addition, 'Sweetcrisp' has smaller berries compared to the berries of 'Southern Belle'. 'Sweetcrisp' differs from the male parent 'FL95-3' (unpatented), in that 'Sweetcrisp' berries have a better picking scar and a higher firmness than 'FL95-3'. In addition, 'Sweetcrisp' flowers and ripens later than 'FL95-3'.

I claim:

1. A new and distinct southern highbush blueberry plant, substantially as illustrated and described, characterized by having a low-chill, vigorous plant with good survival in the field and an extremely firm, sweet berry.

* * * * *

UNITED STATES PATENT AND TRADEMARK OFFICE

CERTIFICATE OF CORRECTION

PATENT NO. : PP 20,027 P3
APPLICATION NO. : 11/288767
DATED : May 26, 2009
INVENTOR(S) : Paul M. Lyrene It is certified that error appears in the above-identified patent and that said Letters Patent is hereby corrected as shown below:

On the title page, below the title, item (50):

"Latin Name: Vaccinium corybosum" should read -- Latin Name: Vaccinium corymbosum --

Signed and Sealed this

Fourth Day of August, 2009

JOHN DOLL
*Acting Director of the United States Patent and Trademark Office*